(12) United States Patent
Orion et al.

(10) Patent No.: US 10,307,164 B2
(45) Date of Patent: Jun. 4, 2019

(54) METHOD FOR CONFIGURING AN ARTERIOVENOUS FISTULA

(71) Applicant: LAMINATE MEDICAL TECHNOLOGIES LTD., Tel Aviv (IL)

(72) Inventors: Eyal Orion, Ramat Efal (IL); Tamar Gilon, Herzlia (IL)

(73) Assignee: Laminate Medical Technologies LTD., Tel Aviv (IL)

(*) Notice: Subject to any disclaimer, the term of this patent is extended or adjusted under 35 U.S.C. 154(b) by 206 days.

(21) Appl. No.: 14/937,889

(22) Filed: Nov. 11, 2015

(65) Prior Publication Data
US 2016/0058453 A1 Mar. 3, 2016
US 2018/0344322 A9 Dec. 6, 2018

Related U.S. Application Data

(60) Division of application No. 14/611,256, filed on Feb. 1, 2015, which is a continuation of application No. PCT/IB2013/056322, filed on Aug. 1, 2013.
(Continued)

(30) Foreign Application Priority Data

Aug. 1, 2012 (WO) .................. PCT/EP2012/065078

(51) Int. Cl.
*A61M 1/36* (2006.01)
*A61B 17/11* (2006.01)

(52) U.S. Cl.
CPC ........... *A61B 17/11* (2013.01); *A61M 1/3655* (2013.01); *A61B 2017/1107* (2013.01); *A61B 2017/1135* (2013.01)

(58) Field of Classification Search
CPC ............ A61B 17/11; A61B 2017/1107; A61B 2017/1135; A61B 2017/1103;
(Continued)

(56) References Cited

U.S. PATENT DOCUMENTS 5,968,089 A 10/1999 Krajíček
6,071,306 A 6/2000 Angelini
(Continued)

FOREIGN PATENT DOCUMENTS

| CN | 2394583 | 9/2000 |
|----|---------|--------|
| CN | 2526019 | 12/2002 |

(Continued)

OTHER PUBLICATIONS

Australian Office Action dated Nov. 14, 2016 for corresponding Application No. 2013298145, filed Mar. 2, 2015.
(Continued)

*Primary Examiner* — Martin T Ton
(74) *Attorney, Agent, or Firm* — Smith, Gambrell & Russell, LLP; Gregory J. Kirsch

(57) ABSTRACT

An embodiment of the invention relates to a method of configuring blood vessels at an anastomosis, the method comprising: ensheathing a segment of a transected first blood vessel in a lumen of a sleeve so that an open end of the segment protrudes from a sleeve end; suturing edges of an incision made in a second blood vessel to the open end of the first blood vessel to create an anastomosis; and sliding the sleeve along the first blood vessel to position the sleeve at the anastomosis.

22 Claims, 8 Drawing Sheets

Related U.S. Application Data

(60) Provisional application No. 61/679,332, filed on Aug. 3, 2012, provisional application No. 61/679,016, filed on Aug. 2, 2012.

(58) Field of Classification Search
CPC ...... A61B 2017/111; A61F 2/064; A61F 2/82; A61F 2002/065; A61M 1/3655
USPC .................................................. 606/153–156
See application file for complete search history.

(56) References Cited

U.S. PATENT DOCUMENTS

| | | | |
|---|---|---|---|
| 6,348,065 B1* | 2/2002 | Brown .................. | A61F 2/91 606/198 |
| 6,972,031 B1* | 12/2005 | Braginsky ............. | A61B 17/12 606/108 |
| 2002/0173809 A1 | 11/2002 | Fleischman et al. | |
| 2003/0225425 A1* | 12/2003 | Kupiecki ............... | A61B 17/11 606/153 |
| 2003/0229365 A1 | 12/2003 | Whayne et al. | |
| 2004/0097988 A1 | 5/2004 | Gittings et al. | |
| 2005/0261713 A1 | 11/2005 | Hassan et al. | |
| 2006/0282106 A1 | 12/2006 | Cole et al. | |
| 2008/0195124 A1 | 8/2008 | Borghi | |
| 2008/0294245 A1 | 12/2008 | Lundh et al. | |
| 2008/0305999 A1 | 12/2008 | Martin et al. | |
| 2009/0024208 A1* | 1/2009 | Barker .................. | A61B 17/11 623/1.35 |
| 2009/0076531 A1 | 3/2009 | Richardson et al. | |
| 2010/0204783 A1 | 8/2010 | Nugent | |
| 2012/0071965 A1* | 3/2012 | Longo .................. | A61B 17/11 623/1.35 |
| 2012/0123451 A1 | 5/2012 | Asfora et al. | |

FOREIGN PATENT DOCUMENTS

| | | |
|---|---|---|
| CN | 102307542 | 1/2012 |
| DE | 10205997 | 9/2003 |
| GB | 2344053 | 5/2000 |
| JP | 2003504166 | 2/2003 |
| JP | 2008522735 | 7/2008 |
| WO | 2010058406 | 5/2010 |
| WO | 2011061493 | 5/2011 |

OTHER PUBLICATIONS

International Search Report for Priority application PCT/EP2012/065078 dated Nov. 7, 2012, filed Aug. 1, 2012.

U.S. Office Action dated Jun. 16, 2016 for corresponding U.S. Appl. No. 14/236,635, filed Mar. 24, 2014.

U.S. Final Office Action dated Jan. 10, 2017 for corresponding U.S. Appl. No. 14/236,635, filed Mar. 24, 2014.

Japanese Office Action dated May 23, 2016 for corresponding Application No. 2014-523323, filed Feb. 3, 2014

European Office Action dated Dec. 2, 2016 for corresponding Application No. 12743153.4, filed Feb. 28, 2014.

Canadian Office Action dated Dec. 23, 2015 for corresponding Application No. 2880343 filed Jan. 28, 2015.

European Office Action dated Aug. 18, 2015 for corresponding Application No. 13762280.90, filed Feb. 27, 2015.

U.S. Office Action dated Jun. 4, 2015 for corresponding U.S. Appl. No. 14/611,256, filed Feb. 1, 2015.

U.S. Office Action dated May 20, 2016 for corresponding U.S. Appl. No. 14/611,256, filed Feb. 1, 2015.

1st Chinese Office Action for Application No. 2013800516184, dated Mar. 21, 2016.

2nd Chinese Office Action for Application No. 2013800516184, dated Nov. 8, 2016.

U.S. Final Office Action dated Dec. 2, 2015 for corresponding U.S. Appl. No. 14/611,256, filed Feb. 1, 2015.

U.S. Final Office Action dated Nov. 16, 2016 for corresponding U.S. Appl. No. 14/611,256, filed Feb. 1, 2015.

International Search Report for PCT/IB2013/056322 dated Nov. 4, 2013.

International Preliminary Report on Patentability dated Nov. 25, 2014.

Roy-Chaudhury et al., "Vascular Access in Hemodialysis: Issues, Management, and Emerging Concepts"; Cardiology Clinics 23, 2005: pp. 249-273.

Japanese Office Action for Application No. 2014-523323, dated Jan. 30, 2017.

U.S. Office Action dated Sep. 6, 2017 for corresponding U.S. Appl. No. 14/236,635, filed Mar. 24, 2014.

U.S. Final Office Action dated Nov. 27, 2017 for corresponding U.S. Appl. No. 14/611,256, filed Feb. 1, 2015.

* cited by examiner

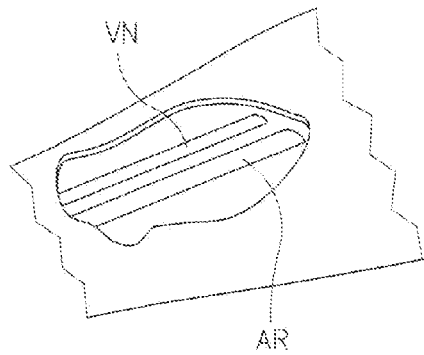
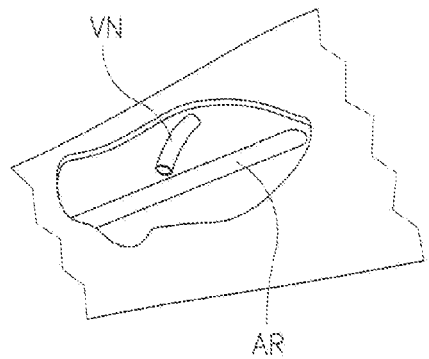
FIG.5A  FIG.5B
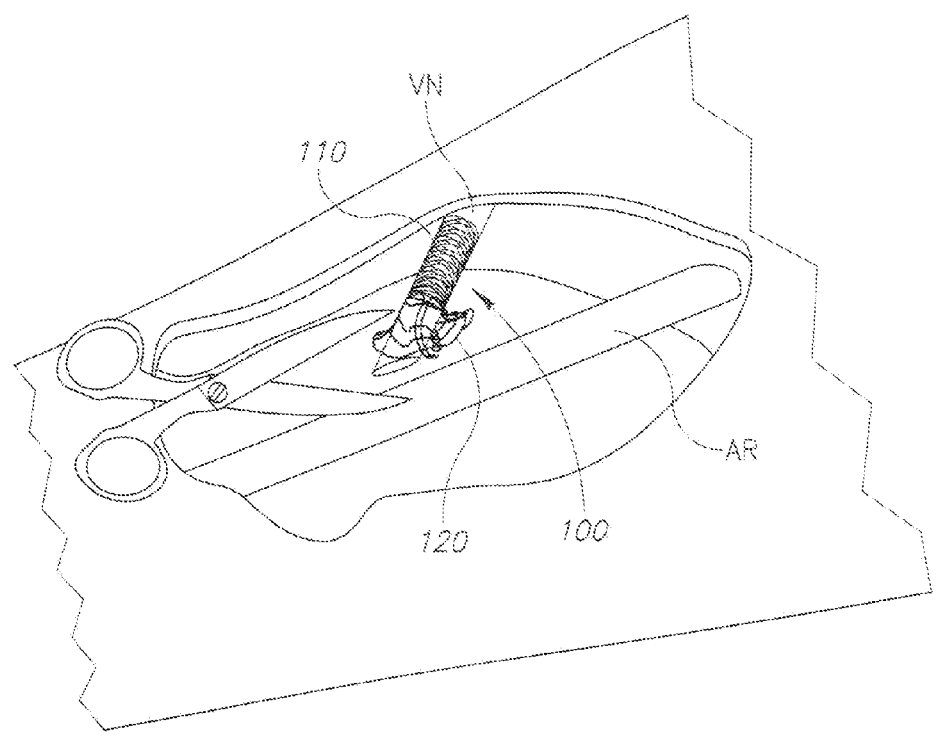
FIG.5C

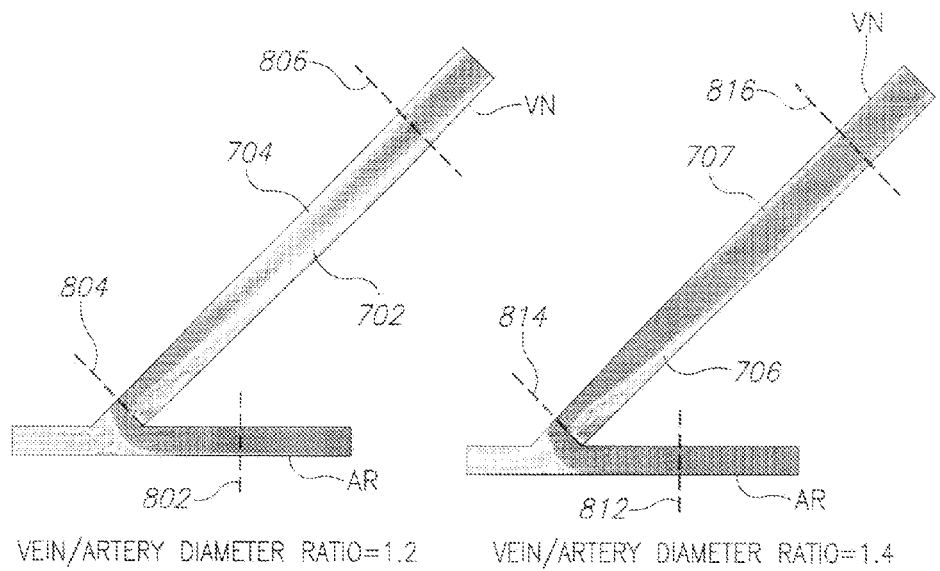
FIG.6A — VEIN/ARTERY DIAMETER RATIO=1.2
FIG.6B — VEIN/ARTERY DIAMETER RATIO=1.4
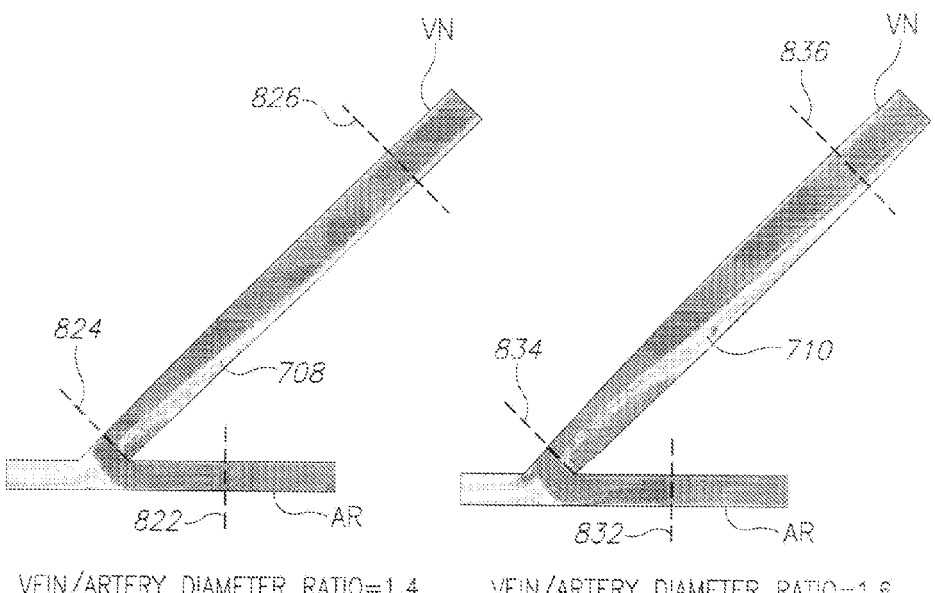
FIG.7A — VEIN/ARTERY DIAMETER RATIO=1.4
FIG.7B — VEIN/ARTERY DIAMETER RATIO=1.6

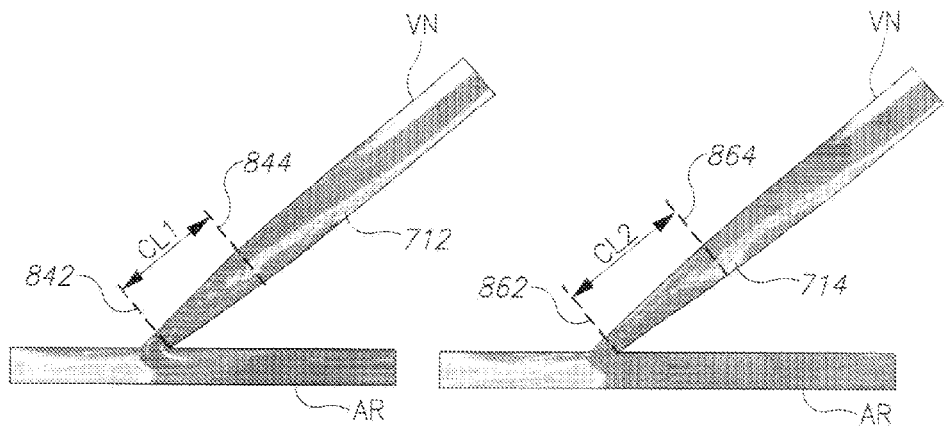
15mm CONICAL
FIG.8A
20mm CONICAL
FIG.8B
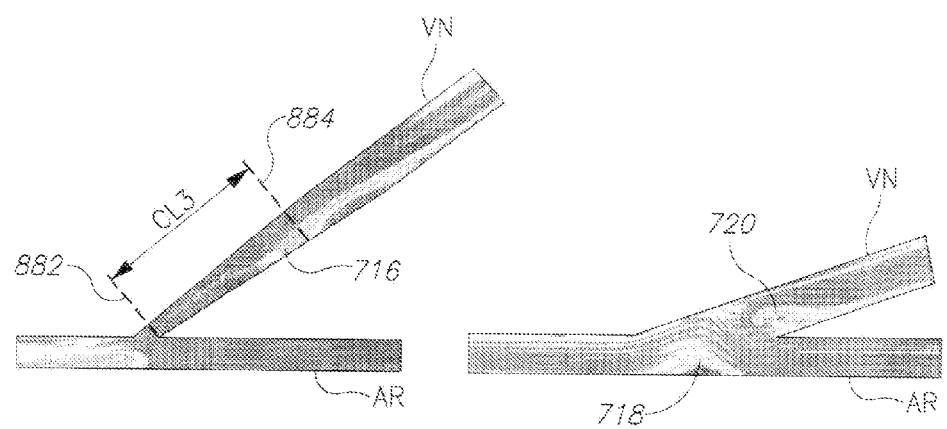
25mm CONICAL
FIG.8C
CONVENTIONAL CONFIGURATION
FIG.9

METHOD FOR CONFIGURING AN ARTERIOVENOUS FISTULA

RELATED APPLICATIONS

The present application is a divisional under 35 U.S.C. 120 of U.S. application Ser. No. 14/611,256 filed Feb. 1, 2015, which is a continuation under 35 U.S.C. 120 of PCT/IB2013/056322 filed on Aug. 1, 2013, which claims benefit under 35 U.S.C. 119(a)-(d) from International Application PCT/EP2012/065078 filed Aug. 1, 2012 as well as benefit under 35 U. S. C. 119(e) from U.S. Provisional Application 61/679,016 filed Aug. 2, 2012 and U.S. Provisional Application 61/679,332 filed Aug. 3, 2012. The contents and disclosures of each of these prior applications are incorporated herein by reference in their entirety.

FIELD

The current disclosure relates to configuring blood vessels in a region of a fistula through which blood flows from one to the other of the blood vessels.

BACKGROUND

Patients with end stage renal disease undergo frequent hemodialysis to remove toxins from the blood and maintain appropriate homeostasis. In dialysis, blood is withdrawn from a vascular access, purified, and returned to a vein or a synthetic graft. The two most common forms designed to enable long-term vascular access in chronic hemodialysis patients are the native arteriovenous (AV) fistula and an AV shunt.

In the AV fistula method, openings are created in an artery and vein, usually in the arm above or below the elbow. The borders of the openings are attached to form an anastomosis at which the vein is joined to the artery and provide a common passageway, conventionally referred to as a fistula, through which blood flows directly from the artery to the vein. The arterial blood pressure, being higher than the venous pressure, together with the supra-physiological flow rates, eventually enlarges the vein and a "mature" and a functioning vascular access is created 2-4 months post procedure. The mature vascular access enables sufficient blood flow rate, effective dialysis procedure and the accommodation of a cannula or large needles.

Hemodialysis vascular access dysfunction is a contributing factor to morbidity in hemodialysis patients. According to Roy-Chaudhury et al., "Vascular access in hemodialysis: issues, management, and emerging concepts" (in Cardiology Clinics 23, 2005: 249-223) there are several causes of failures of vascular access procedures. Roy-Chaudhury et al. identifies two main causes of such failure in AV fistulae as maturation failure and early venous stenosis, both are caused by development of neointimal hyperplasia which includes thickening of the tunica media and the tunica intima (a smooth muscle wall and endothelial layer in the vessel) due to inward proliferation of cells.

Maturation failure and early venous stenosis may be caused by the development of a juxta-anastomotic stenosis due to the neointimal hyperplsia in propinquity to the artery-vein anastomosis. According to Roy-Chaudhury et al., an initiating event in the pathogenesis of venous stenosis in AV dialysis is hemodynamic stress, especially in regions of low shear stress and turbulence in the vicinity of the fistula. Another initiating event is the high wall tension to which the vein graft is exposed. Under normal physiological conditions, the pressure in the venous circulation is 3-5 mmHg After fistula creation, the mean pressure in the vein is 100 mmHg Unlike arteries, veins have relatively thin wall with thin muscularis layer. As a compensation reaction, while trying to adapt to the "new" physiological conditions and high pressures, the vein wall thickens in an attempt to reduce the sudden high wall tension. The pathological process of wall thickening is considered the seed of intimal hyperplasia and vein stenosis.

SUMMARY

An aspect of an embodiment of the invention relates to providing an apparatus or a system, also referred to as a "fistula join", to provide and maintain a desirable configuration of native blood vessels or a native blood vessel and an artificial blood conduit in the vicinity of a fistula through which blood flows from one to the other of the blood vessels or between the conduit and the native blood vessel. For convenience of presentation a native blood vessel and a blood conduit are generically referred to as a blood vessel.

As used herein, the "fistula" refers to the plane of the opening through which the blood from a first blood vessel flows to a second blood vessel. The fistula may be, for example, created through the process of anastomosis. The "vicinity of the fistula", as used herein, refers to at least the portion of the first and second blood vessels apposed to, enclosed within, ensheathed within or within the lumen of a fistula join or components thereof.

According to an embodiment of the invention, a fistula join comprises a coupler that couples to a first of a pair of blood vessels joined at a fistula and a restrictor sleeve (alternatively referred to herein as a "sleeve") that ensheathes a second of the pair of blood vessels. The coupler optionally comprises a mount and an adapter. The mount seats on the first blood vessel and surrounds at least a portion of the first blood vessel. The mount may comprise at least one brace that can be closed to prevent the coupler, once seated on the first blood vessel, from lifting off from the first blood vessel. Optionally, the mount has a shape reminiscent of a saddle and the at least one brace comprises two opposing braces that may be joined to "strap" the mount and thereby secure the coupler to the first blood vessel. The adapter extends from the mount and is configured to mate and fasten to the restrictor sleeve that ensheathes the second blood vessel. The adapter may have a collar like shape that fits over or inside the restrictor sleeve. Optionally, the restrictor sleeve is integrally formed as an extension of the adapter.

In an embodiment of the invention, the adapter is configured to hold the restrictor sleeve and thereby the second blood vessel in the vicinity of the fistula substantially at a desired acute angle relative to a direction along which the portion of the first blood vessel to which the coupler is attached extends. The desired acute angle may hereinafter be referred to as a "fistula join angle", or a "join angle". The coupler may be configured to constrain the portion of the first blood vessel to which it is mounted, or the portion of the second blood vessel in the vicinity of the fistula that is substantially contained within the lumen of the adapter, to a desired shape, hereinafter also referred to as a "first constrained shape". The restrictor sleeve may be configured to limit strain or wall tension generated by blood pressure in the portion of the second blood vessel that the sleeve ensheathes. Additionally, the restrictor sleeve may be configured to constrain the second blood vessel portion to a desired shape or size. The desired shape or size of the ensheathed blood vessel may hereinafter be referred to as a "second constrained shape".

In an embodiment of the invention, the fistula join is configured to provide a desired flow pattern of blood through the fistula and in regions of the first and second blood vessels in the vicinity of the fistula. Configuring the fistula join may comprise configuring any one or combination of at least two of the coupler mount, the coupler adapter or the restrictor sleeve. Configuring the fistula join may be performed to configure any one or any combination of two or more of the join angle, the first constrained shape, and the second constrained shape. In an embodiment of the invention, the fistula join may be configured to enhance laminar flow of blood through the fistula and/or in at least one of the first and second blood vessels in the vicinity of the fistula. Optionally, the fistula join is configured to moderate blood pressure in the first or second blood vessel.

In an embodiment of the invention, the fistula is an arteriovenous fistula that provides direct blood flow from an artery to a vein and the fistula join is adapted to configure the vein and artery in the vicinity of the fistula. The first blood vessel, to which the coupler, optionally referred to as the "artery coupler", is attached, is the artery, optionally referred to as the "fistula artery". The second blood vessel that the restrictor sleeve ensheathes is the vein, optionally referred to as the "fistula vein". The restrictor sleeve may be referred to as a "venous restrictor sleeve". The fistula join comprising the artery coupler and the venous restrictor sleeve may be referred to as an arteriovenous fistula join.

In an embodiment of the invention, the join angle of the arteriovenous fistula join is between about 20° and about 60°.

In an embodiment of the invention, the venous restrictor sleeve, which is oriented at the join angle, may ensheathe a length of from about 10 mm to about 30 mm of the vein. Optionally the restrictor sleeve has a constant cross section. The restrictor sleeve may have a cross section that changes as a function of distance along the sleeve. Optionally, the cross section increases with distance along the vein from the fistula. The diameter of the restrictor sleeve outlet distal from the fistula may be larger than the diameter of the restrictor sleeve inlet proximal to the fistula. The ratio of the outlet diameter to the inlet diameter may be between about 1.3 and about 1.5. Optionally, the inlet may assume a substantially circular cross section having an internal diameter substantially equal to or greater than an external diameter of the first blood vessel. Optionally, the restrictor sleeve has a mixed conical/cylindrical shape, having a conical segment proximal to the fistula having a cross section that increases with distance from the fistula and a cylindrical segment distal from the fistula having a constant cross section. Optionally, the conical segment may comprise between about 50% and about 80% of the restrictor sleeve along its longitudinal axis, with the remainder of the restrictor sleeve being cylindrical in shape. Optionally, the conical segment may be between about 10 mm and about 25 mm in length.

Arteriovenous fistula joins characterized by join angles and restrictor sleeve dimensions in accordance with an embodiment of the invention may provide advantageous Reynolds numbers and corresponding improved laminar blood flow through a fistula at an anastomosis between an artery and a vein. In an embodiment of the invention, the Reynolds number is less than about 1500.

Another aspect of an embodiment of the invention relates to a method for providing external support to an arteriovenous fistula comprising the steps of: providing a fistula join comprising a coupler connected to a restrictor sleeve; transecting a vein and selecting the vein segment leading to the heart; passing the vein segment completely through the lumen of the fistula join so that the transected end of the vein segment protrudes from the coupler; anastomosing the protruding end of said vein segment to the side of an artery to create an arteriovenous junction; and passing the fistula join along the vein segment so that coupler is in contact and nested upon a portion of the artery adjacent to or surrounding the fistula.

There is therefore provided in accordance with an embodiment of the invention, apparatus for configuring first and second blood vessels connected by an anastomosis at a fistula, the apparatus comprising: a coupler that seats on and couples to the first blood vessel; and a sleeve connected to the coupler that ensheathes and holds a portion of the second blood vessel in the vicinity of the fistula so that an acute join angle formed between the first and second blood vessels at the fistula is greater than about 20°. Optionally, the join angle is less than about 60°. Additionally or alternatively, the sleeve has a cross section that is a function of distance along the sleeve from the coupler.

There is further provided in accordance with an embodiment of the invention, apparatus for supporting first and second blood vessels connected by an anastomosis at a fistula, the apparatus comprising: a coupler that seats on and couples to the first blood vessel; and a sleeve connected to the coupler that ensheathes a portion of the second blood vessel in the vicinity of the fistula and has a cross section that is a function of distance along the sleeve from the coupler.

In an embodiment of the invention, the sleeve assumes a substantially circular cross section proximal to the fistula having an internal diameter substantially equal to or greater than an external diameter of the first blood vessel.

In an embodiment of the invention, the cross section of the sleeve increases as a function of distance from the coupler along the sleeve for at least a first portion of the sleeve length, beginning from the sleeve opening proximal to the fistula. Additionally or alternatively, the first portion is greater than or equal to about 50% of the total sleeve length. The first portion is optionally greater than or equal to about 60% of the total sleeve length. The first portion is optionally less than or equal to about 80% of the total sleeve length. Additionally or alternatively, the first portion is equal to or greater than about 10 mm in length. The first portion is optionally equal to or greater than about 15 mm in length. The first portion is optionally less than or equal to about 20 mm in length. Additionally or alternatively, the diameter at the larger opening of the sleeve is greater than or equal to about 1.3 times the diameter at the smaller opening of the sleeve. Optionally, the sleeve is greater than or equal to about 1.4 times the diameter at the smaller opening of the sleeve. Optionally, the diameter at the larger opening of the sleeve is less than or equal to about 1.5 times the diameter at the smaller opening of the sleeve. Additionally or alternatively, the sleeve has a second portion that extends from an end of the first portion to an end of the sleeve and has a substantially same cross section at each point along its length.

In an embodiment of the invention, the sleeve has a length equal to or greater than about 15 mm Optionally, the sleeve has a length equal to or greater than about 20 mm Optionally, the sleeve has a length equal to or greater than about 25 mm Optionally, the sleeve has a length equal to or less than about 30 mm.

In an embodiment of the invention, the coupler comprises a brace that can be closed to prevent the coupler from lifting off from the first blood vessel.

In an embodiment of the invention, the coupler is operable to impose a rounded contour to at least a portion of the first or second blood vessel apposed to the coupler. Optionally, the coupler is operable to impose a rounded contour to the portion of the first or second blood vessel at the acute angle formed by the junction of the first and second blood vessels.

In an embodiment of the invention, the first blood vessel is an artery. The artery is optionally a brachial artery or a radial artery.

In an embodiment of the invention, the second blood vessel is a vein. The vein is optionally a cephalic vein.

There is further provided in accordance with an embodiment of the invention, a method of configuring blood vessels at an anastomosis, the method comprising: making an incision having edges in a first blood vessel; transecting a second blood vessel to provide a blood vessel segment having an open end; ensheathing the segment in a sleeve so that the open end protrudes from the sleeve; suturing the open end to edges of the incision to form a fistula; sliding the sleeve along the second blood vessel to position the sleeve at the anastomosis; and coupling the sleeve to the first blood vessel so that the sleeve configures a portion of the second blood vessel that extends from the fistula. Optionally, the incision in the first blood vessel is made before transecting the second blood vessel. Optionally, the incision in the first blood vessel is made after transecting the second blood vessel. Optionally, the incision in the first blood vessel is made after ensheathing the segment of the second blood vessel in the sleeve.

Additionally or alternatively, coupling the sleeve comprises suturing or gluing a portion of the sleeve to the first blood vessel Additionally or alternatively, coupling the sleeve comprises seating onto the first blood vessel a coupler previously connected to the end of the sleeve proximal to the fistula. Optionally, coupling the sleeve further comprises closing a brace incorporated into the coupler around the first blood vessel.

In the discussion, unless otherwise stated, adverbs such as "substantially", "approximately" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF FIGURES

Non-limiting examples of embodiments of the invention are described below with reference to figures attached hereto that are listed following this paragraph. Identical structures, elements or parts that appear in more than one figure are generally labeled with a same numeral in all the figures in which they appear. A label labeling an icon representing a given feature of an embodiment of the invention in a figure may be used to reference the given feature. Dimensions of components and features shown in the figures are chosen for convenience and clarity of presentation and are not necessarily shown to scale.

FIGS. 5A-E schematically illustrate steps of a method for providing external support to an arteriovenous fistula in accordance with some embodiments of the present invention;

FIGS. 6A-B show the visualization of blood flow at a simulated arteriovenous junction, characterized by different vein/artery diameter ratios;

FIGS. 7A-B show the visualization of blood flow at a simulated arteriovenous junction, characterized by different vein/artery diameter ratios;

FIGS. 8A-C show the visualization of blood flow in a simulated arteriovenous junction, characterized by different sizes of an initial conical segment in the vein; and FIG. 9 shows the visualization of blood flow in a simulated arteriovenous junction in a conventional configuration.

DETAILED DESCRIPTION

Figure 1A:
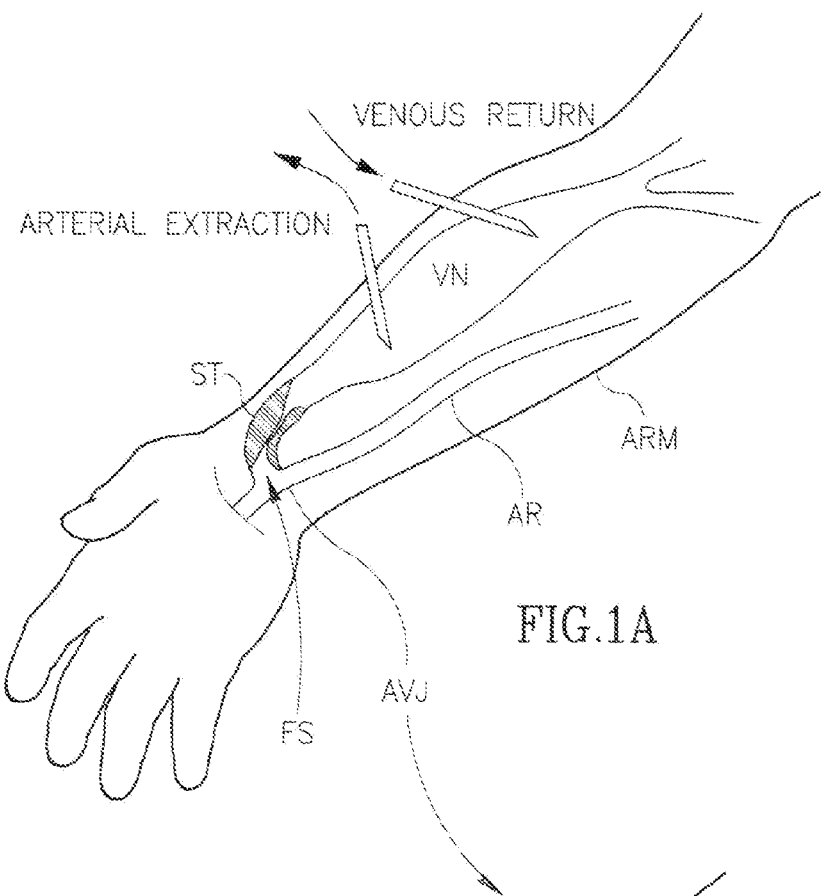
FIGS. 1A-B schematically illustrate an arteriovenous junction with a fistula in an arm.
Figure 1B:
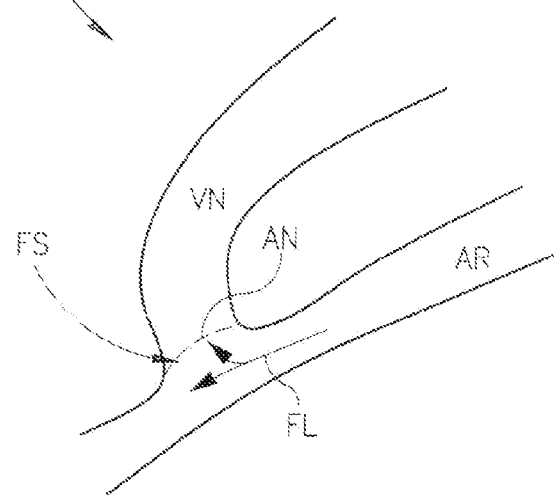
Figure 2A:
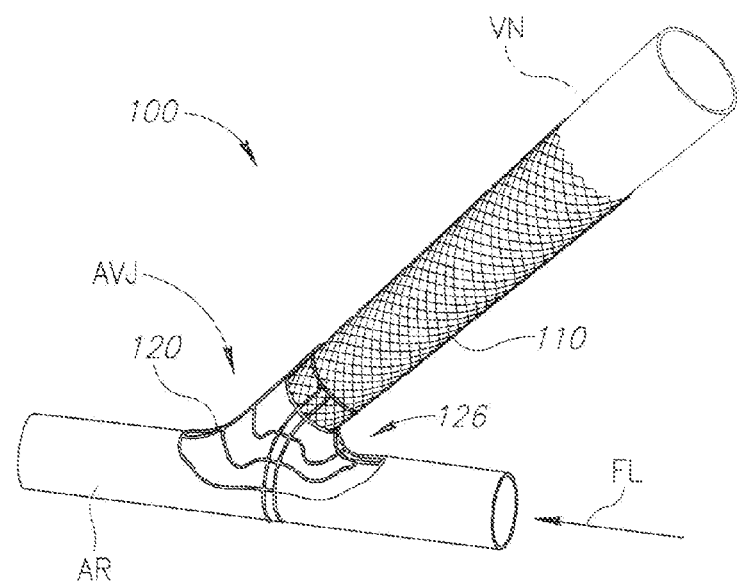
FIGS. 2A-B schematically illustrate an exemplary fistula join having a coupler and a restrictor sleeve for modifying an arteriovenous fistula, in accordance with some embodiments of the present invention.
Figure 2B:
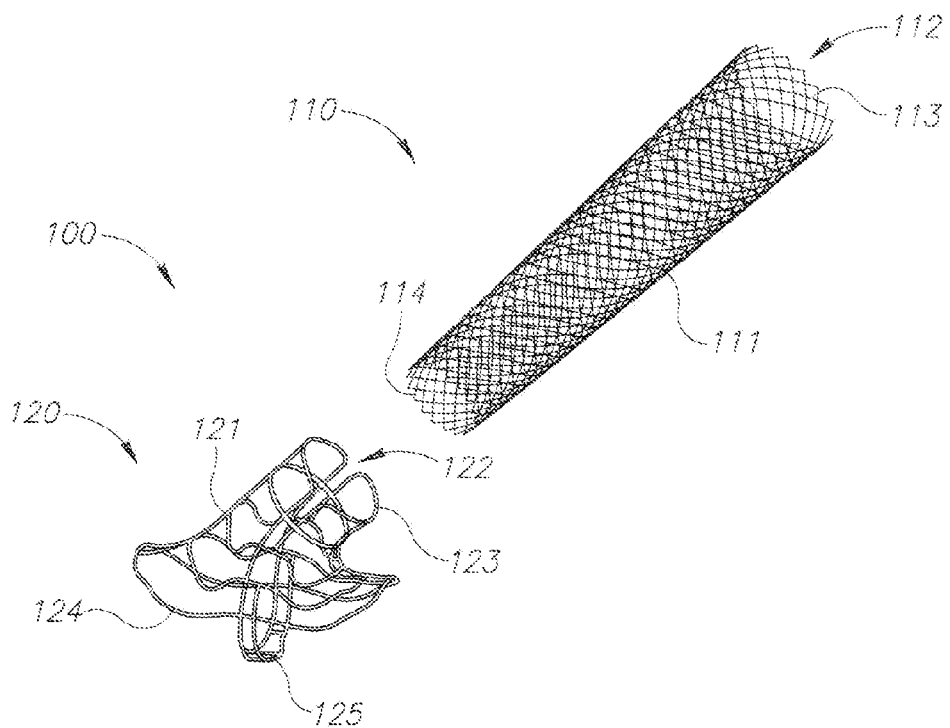
Figure 3:
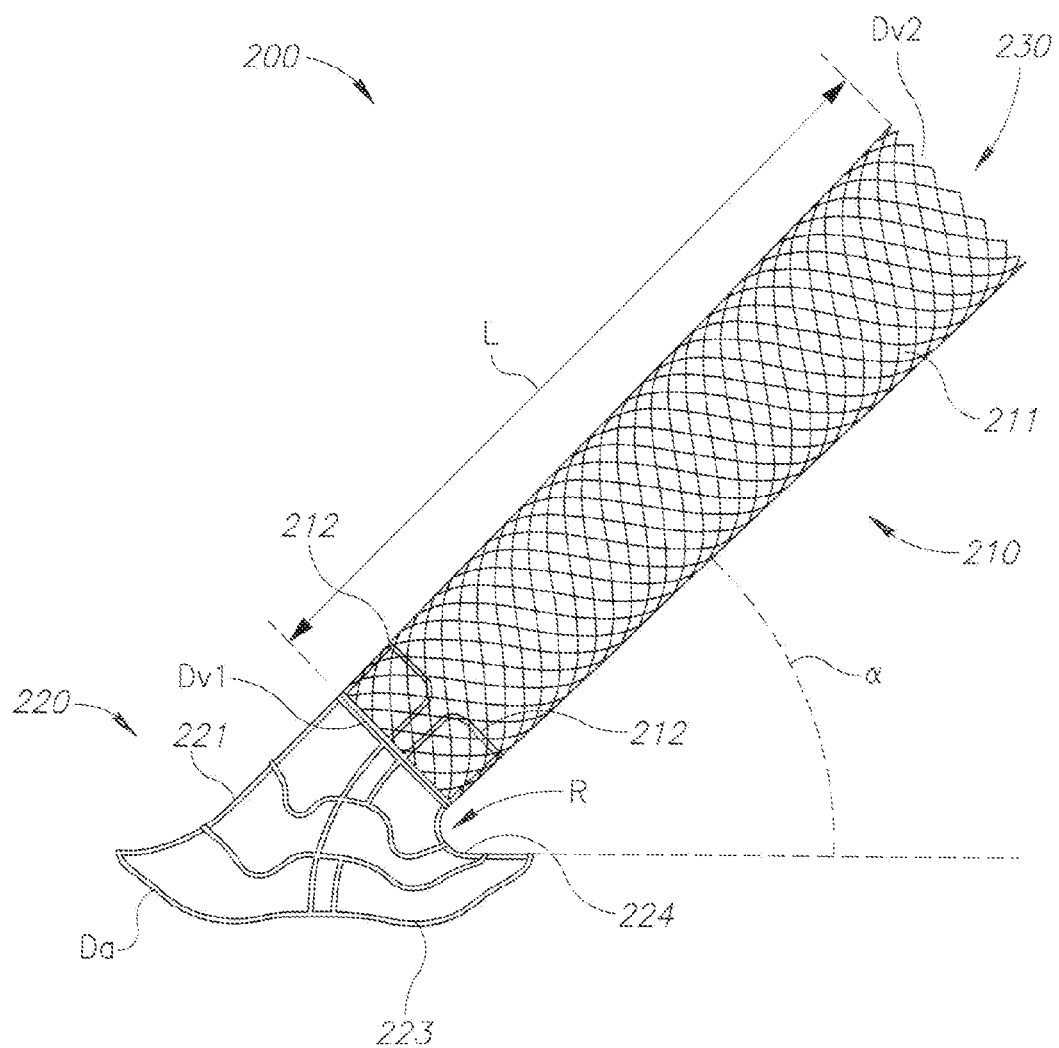
FIG. 3 schematically illustrates an exemplary fistula join having a coupler and a restrictor sleeve, in accordance with some embodiments of the present invention.

The present invention, in some embodiments thereof, relates to external vascular supports and in particular to external supports for arteriovenous junctions. In the following detailed description, the components of an exemplary arteriovenous junction and features of its maturation are schematically illustrated in FIGS. 1A-B and discussed with reference to those figures. Examples of a fistula join having a coupler and/or a restrictor sleeve in accordance with embodiments of the invention are schematically illustrated in FIGS. 2A-B and FIG. 3, and discussed with reference to the figures. Examples of a coupler in accordance with embodiments of the invention are shown in perspective views in FIGS. 4A-C and discussed with reference to the figures. Steps of a method for providing external support to an arteriovenous junction using a fistula join in accordance with embodiments of the invention are shown in FIGS. 5A-E and discussed with reference to the figures. Images of computer simulations of blood flow from an artery through a fistula to a vein in regions of anastomosis joining the artery and vein are shown in FIGS. 6A-B and FIGS. 7A-B, and discussed with reference to the figures. Images of computer simulations of blood flow from an artery through a fistula to a vein, with the initial vein segment proximal to the fistula shaped as various combinations of cone-like and cylinder-like segments, are shown in FIGS. 8A-C and discussed with reference to the figures. An image of a computer simulation of blood flow from an artery through a fistula to a vein in a conventional arteriovenous junction is shown in FIG. 9.

The following embodiments may be described in the context of exemplary external support systems for arteriovenous junctions that are prepared in patients to facilitate hemodialysis, for convenience of description and understanding. However, embodiments of the invention are not limited to the specifically described devices and methods, and embodiments may be adapted to various clinical applications without departing from the overall scope of the invention. For example, devices and related methods including concepts described herein may be used for preventing and/or treating intimal hyperplasia or remodeling in other manmade anatomical junctions, including end-to-side, end-to-end or side-to-side anastomoses, in vasculatures or other organs.

FIGS. 1A-B schematically illustrate an arteriovenous junction, AVJ, forming a fistula FS in an arm. Arteriovenous junction AVJ is surgically prepared by the procedure of anastomosis, where the open end of vein VN is connected to a side of an artery AR having an arteriotomy, thus providing a common passageway, conventionally referred to as a fistula, through which blood flows directly from artery AR to vein VN. As used herein, in the context of an arteriovenous junction, fistula FS refers in particular to the opening of the common passageway at the side of artery AR. It will be appreciated that the location of the fistula FS may be independent of the precise location of the junction between arterial tissue and venous tissue. Depending on the particulars of the anastomosis procedure and/or how the vascular walls heal and mature over time, the vascular wall at the fistula may be arterial, venous, or a combination thereof. Where vein VN joins artery AR at arteriovenous junction AVJ at an angle other than a right angle, the fistula FS may be shaped substantially as an ellipse. Typically, but not necessarily, the minor axis of the ellipse may be substantially equal to a diameter of artery AN at or in the vicinity of the fistula.

FIG. 1A shows the arm with fistula vein VN in a mature stage. Fistula vein VN connected to artery AR through fistula FS matures over months following the anastomosis procedure. Fistula vein VN, once fully developed, becomes enlarged and suitable for introductions of needles or cannulae for connecting with an external hemodialysis system used for arterial extraction of blood with waste products and venous return of filtered blood. However, concomitant with the maturation of fistula vein VN, stenosis ST may also develop, reducing blood flow and blood pressures into fistula vein VN.

FIG. 1B shows an enlarged view of arteriovenous junction AVJ with fistula FS at an earlier stage, for example immediately following fistula FS formation through anastomosis AN of a fistula vein VN with an artery AR. Blood flow FL flowing downward via artery AR now enters, completely or partly, into fistula vein VN via fistula FS. At this stage, stenosis is absent. Fistula vein VN may be somewhat expanded, even at initial stages prior to fistula vein maturation, due to the high arterial pressure it now houses.

FIGS. 2A-B schematically illustrate an exemplary fistula join system 100. Fistula join 100 includes a coupler 120. Optionally, fistula join 100 further includes a restrictor sleeve 110 connectable to coupler 120. In certain alternative embodiments, fistula join 100 may include restrictor sleeve 110 without coupler 120.

Coupler 120 includes a mount 124 having a first shape, an adapter 123 having a second shape, and an intermediate portion 121 shaped such that it gradually alters in shape from the first shape to the second shape. A lumen 122 passes through coupler 120 and is configured to directly communicate with lumen 112 when coupler 120 and restrictor sleeve 110 are connected correctly.

Mount 124 is shaped to nest over a rounded artery portion AR adjacent arteriovenous junction AVJ. In order to substantially coincide over artery portion AR, mount 124 includes a saddle-like shape sized to accommodate artery AR diameter along a substantial length, thereby providing sufficient support to maintain a desirable configuration of the fistula at the arteriovenous junction, as well as the portions of the anastomosed vein and artery in the vicinity of the fistula. Mount 125 may also provide sufficient support to secure a restrictor sleeve 110 at a determined alignment, orientation or angle.

Mount 124 may further include a brace 125, which may for example include two legs configured to be closable in order to prevent coupler 120, once seated on artery AR, from lifting off from artery AR. The legs may be elastic and form a non-stressed ring-like shape having a chosen diameter, which could be substantially the same as of artery AR, slightly larger or slightly smaller. The closing of brace 125 may be secured with or without additional suturing or bonding. Additionally, brace 125 may be operable to deform the geometrical configuration of the fistula and the surrounding vascular wall, which deformation may be operable to improve blood flow at or near the deformation.

Adapter 123 extends from mount 124 and is connectable with restrictor sleeve 110. Adapter 123 may comprise a cylindrical shape enclosing a diameter being equal to or greater than the external diameter of a fistula vein segment inserted therein. The end of the cylindrical shape may have a collar-like shape that fits over or inside inlet 114 of restrictor sleeve 110. Adapter 123 may be connectable with inlet 114 of restrictor sleeve 110, optionally, by means of one or more of: mechanical tension, a mechanical interlocking mechanism, welding, bolting, snap-locking, threading, soldering or gluing. In certain embodiments of the invention, the diameter of adapter 123 and inlet 114 may be substantially equal, albeit with the diameter of one being slightly larger or smaller than the other to allow the adapter 123 to fit over or inside inlet 114. Optionally, the adapter 123 or inlet 114 may assume a substantially circular cross section having an internal diameter substantially equal to or greater than an external diameter of the artery.

Restrictor sleeve 110 and coupler 120 may be connected before, during or after implantation and deployment onto the arteriovenous junction or the fistula vein. In a preferred embodiment of the invention, coupler 120 and restrictor sleeve 110 are connected prior to deployment. Alternatively, restrictor sleeve 110 may be integrally formed as an extension of adapter 123.

Coupler 120 as a whole may be shaped such that, when mount 124 is seated on the surface of artery AR, the longitudinal axes of adapter 123 and restrictor sleeve 110 (which typically overlap) are secured at a desired angle with respect to the longitudinal axis of artery AR. Optionally, the acute angle defined thereby ("the join angle") is between about 20° and about 60°. In exemplary embodiments of the invention, the join angle is about 40°.

Coupler 120 may be configured to constrain a portion of artery AR to which it is mounted, or the portion of the fistula vein in the vicinity of the fistula that is substantially contained within the lumen of adapter 123, to a first constrained shape. In certain embodiments of the invention, intermediate portion 121 may induce the formation of a desired rounding at the fistula or the nearby blood vessel portions by providing a fixed rounded contour 126. For example, the intermediate portion 121 may induce a rounding of the blood vessel wall, or to impose a rounded contour, at the acute angle formed at the junction of the connected blood vessels. The first constrained shape may achieve improved blood flow at or near the fistula. Such improved flow characteristics may include diminished turbulent flow, increased hemodynamic shear stress, and/or decreasing the average Reynolds number of the blood flow, e.g., to less than 1500, or to between about 150 to about 1000.

Coupler 120 may be constructed out of a biocompatible material such as stainless steel, titanium, polymers, or synthetic yarns. The stainless steel may comprise, for example, Co—Cr or Ni—Ti alloys. Preferably, the coupler allows for osmosis at the wall of the first blood vessel to continue. As such, the biocompatible material may be semi-permeable, or constructed with gaps, holes, or the like to keep exposed a substantial portion of the enclosed blood vessel. As such, the coupler may be formed from a metal piece having a plurality of slender struts defining openings therebetween. The metal may be formed by, e.g., machining, casting, forging, laser cutting and like, or a combination thereof. In exemplary embodiments of the invention, coupler 120 may be laser cut from a Ni—Ti alloy solid and include a plurality of slender struts defining openings therebetween.

Restrictor sleeve 110 includes an elongated tubular body 111 with an outlet 113, an inlet 114 and a lumen 112 passing along its length and open at both ends. Restrictor sleeve 110 is configured to be deployed to ensheathe a blood vessel, for example a vein, such that the a portion of the blood vessel is enclosed within lumen 112 (or alternatively stated, covered by restrictor sleeve 110). Inlet 114 refers to the open end of the restrictor sleeve that is oriented towards (and thus is proximal to) the fistula when the vein is anastomosed to an artery. Outlet 113 refers to the open end of restrictor sleeve 110 that is oriented away from (and thus is distal from) the fistula when the vein is anastomosed to an artery. Typically, after the anastomosis is performed, arterial blood flow first enters the portion of the vein covered by inlet 114 of restrictor sleeve 110, and then exits out of the portion of the vein covered by outlet 113 of restrictor sleeve 110.

Restrictor sleeve 110 may be a few centimeters in length, optionally between about 1 cm and about 4 cm or between about 2 cm and about 3 cm. In exemplary embodiments of the invention, restrictor sleeve 110 may be about 2.5 cm in length. Restrictor sleeve 110 may be positioned on the fistula vein to begin a few millimeters, up to a few centimeters, from the fistula along the vein, optionally between about 1 mm and about 50 mm, between about 2 mm to about 30 mm or between 5 mm to about 15 mm.

Restrictor sleeve 110 may have a fixed length or can be stretched up to a chosen length, before, after or during deployment over the vein segment. The width of lumen 112 may be adjusted to constrict the vein segment to final external boundaries immediately at deployment, or the width of lumen 112 may be oversized and designed to allow the vein segment to expand, up to the final external boundaries restricted by the restrictor sleeve 110. Restrictor sleeve 110 may be configured to substantially withstand radial expansion over a predetermined diameter.

Restrictor sleeve 110 may be compressible. Restrictor sleeve 110 may be operable to be configured in a stressed state that is shorter with respect to its relaxed length by at least 20%, optionally at least 30%, optionally at least 50%, or higher, or lower, or to an intermediate percentage. Optionally in addition, the width of lumen 112 may be wider in the stressed state by at least 20%, optionally at least 30%, optionally at least 50%, or higher, or lower, or to an intermediate percentage.

In some embodiments of the invention, tubular body 111 has a cylinder-like ("cylindrical") shape. In some embodiments of the invention, tubular body 111 includes a cone-like ("conical") shape with a cross section that increases with distance from the fistula, thus having a narrower diameter at inlet 114 and a wider diameter at outlet 113. The diameter of outlet 113 may be between about 1.2 and about 1.8 times the diameter of inlet 114, or between about 1.3 and about 1.4 times the diameter of inlet 114. In exemplary embodiments of the invention, the diameter of outlet 113 is about 1.4 times the diameter of inlet 114. As used herein, a cone-like or conical shape is not limited to a shape that exactly conforms to a geometric cone or a truncated cone, but to any shape having a cross section that increases with distance along an axis. The cone-like or conical shape may be a frustum (e.g., a cone, a paraboloid, hyperboloid or a neiloid) or an asymmetric shape.

In some embodiments of the invention, tubular body 111 has a mixed conical/cylindrical shape, with a conical segment proximal to the fistula, followed by a cylindrical segment distal from the fistula. Where tubular body 111 is of the mixed conical/cylindrical shape, the conical segment may comprise between about 50% and about 100% of the restrictor sleeve along its longitudinal axis. Alternatively or in combination, the conical segment may optionally be between about 5 mm and about 35 mm or between about 10 mm and about 25 mm. In exemplary embodiments of the invention, the conical segment comprises about 60% of the restrictor sleeve along its longitudinal axis, with the remaining 40% being cylindrical in shape. In exemplary embodiments of the invention, the conical segment is about 15 mm in length. In exemplary embodiments of the invention, restrictor sleeve 110 is about 25 mm in length, having a conical segment of about 15 mm in length and a cylindrical segment of about 10 mm in length.

Restrictor sleeve 110 may be constructed out of a biocompatible material such as stainless steel, titanium, polymers, or synthetic yarns. The stainless steel may comprise, e.g., Co—Cr or Ni—Ti alloys. Preferably, restrictor sleeve 110 allows for osmosis at the wall of the first blood vessel to continue. As such, the biocompatible material may be semi-permeable, or constructed with gaps, holes, or the like to keep exposed a substantial portion of the enclosed blood vessel. In a preferred embodiment of the invention, tubular body 111 is meshed in order to allow cell ingrowths through its openings and therefore allow impregnation of the body with the remodeled blood vessel over time. In some embodiments of the invention, tubular body 111 is braided. In some embodiments of the invention, tubular body 111 is made by intertwining of three or more wires or fibers, optionally 10 or more intertwined wires or fibers, optionally thirty or more intertwined wires or fibers. In some embodiments of the invention, wires are used which are made of stainless steel, optionally of a Ni—Ti alloy. In some embodiments of the invention, wire diameter is in the range of 1 micron to 1 mm, optionally 1 micron to 100 microns, or optionally 30 microns to 60 microns. In exemplary embodiments of the invention, tubular body 111 comprises a braid having 42 intertwined Ni—Ti alloy wires, each approximately 45 microns, or optionally and particularly 43 microns, in diameter. Optionally the braid has a braiding angle (i.e., an angle formed between two adjacent intertwined wires along a longitudinal axis of the braid) when in a relaxed (unstressed) form that is 90° or higher, optionally 100° or higher, optionally 120° or higher.

Restrictor sleeve 110 may be configured to constrain the second blood vessel portion to a desired second constrained shape. The second constrained shape may be operable to improve blood flow characteristics in and around the portion of the fistula vein ensheathed by restrictor sleeve 110. Such improved flow characteristics may include diminished turbulent flow, increased hemodynamic shear stress, and/or decreasing the average Reynolds number of the blood flow, e.g., to less than 4000, less than 2000, less than 1500, or to between about 150 and about 1000.

The arteriovenous junction to which fistula join 100 is associated may be a cephalic vein anastomosed to a radial artery (to form a radiocephalic fistula at the forearm) or to a brachial artery (to form a brachiocephalic fistula at the elbow). The dimensions of fistula join 100, including coupler 120 or restrictor sleeve 110, may depend on the external diameter of the blood vessels being anastomosed. The external diameter of the blood vessels being anastomosed may depend on the particular blood vessels being used, and on the individual being treated. In certain embodiments of the invention, the external diameter of the artery may optionally be between about 2 mm and about 6 mm or between about 3 mm and about 5 mm. For example, in case of the radiocephalic fistula, using restrictor sleeve 110 having an inlet 114 diameter between 2.4 mm and 3.6 mm and an outlet 113 diameter between 2.5 mm and 6.5 mm may be appropriate. Alternatively, in the case of a brachiocephalic fistula, restrictor sleeve 110 having an inlet 114 diameter between 3.6 mm and 4.8 mm and an outlet 113 diameter between 3.7 mm and 11.7 mm may be appropriate. The dimensions of other portions or components of the fistula join may be similarly adjusted, in accordance with the dimensions of the blood vessels.

In certain embodiments of the invention, the portion of the fistula vein proximal to the fistula may be prone to narrowing (for example, due to stenosis and/or neointimal hyperplasia). Fistula join 100 may be operable to prevent, treat or mitigate stenosis and/or neointimal hyperplasia in the fistula vein at or near the portion of the fistula vein that is externally supported by fistula join 100. Fistula join 100 may operable to prevent, treat or mitigate stenosis through, for example, improving blood flow, reducing turbulence or increasing hemodynamic shear stress, as well as by reducing fistula vein wall tension, which may be caused by exposure to arterial blood pressure. In addition to improving blood flow and reducing wall tension, fistula join 100 may be operable to restrict the expansion of at least the portion of the fistula vein within the lumen of coupler 120 or restrictor sleeve 110 to within predetermined boundaries. A certain amount of expansion in the fistula vein may be desired. However, excessive expansion of the fistula vein proximal to the fistula may result in insufficient downstream peripheral blood flow (for example, steal syndrome, also known as vascular access steal syndrome or dialysis-associated steal syndrome). As such, fistula join 100 may be operable to prevent, treat or mitigate steal syndrome.

FIG. 3 schematically illustrates an exemplary fistula join 200, comprising a restrictor sleeve 210 and a coupler 220. Restrictor sleeve 210 may be similar or identical to restrictor sleeve 110. Coupler 220 may be similar to coupler 120, or even identical in any or all geometries and/or features. Optionally, coupler 220 does not include a brace for embracing an artery. In such a case, coupler 220 may be connectable to the fistula artery and/or to an arteriovenous junction having a fistula by any one or a combination of various methods known in the art, such as suturing or bonding.

Restrictor sleeve 210 may be shaped as a braided truncated cone made of intertwined stainless steel (for example, Ni—Ti alloy) wires, having an inlet 212 enclosing a smaller diameter $Dv1$ and an outlet 211 enclosing a greater diameter $Dv2$, and a lumen 230 passing therealong sized and configured to enclose a fistula vein segment having a length L. The fistula vein segment ensheathed within restrictor sleeve 210 may be at risk of developing neointimal hyperplasia and/or stenosis or be excessively widened to induce steal syndrome. Optionally, length L is 10 mm to 50 mm, about 30 mm, about 25 mm, or about 20 mm. The longitudinal axis of restrictor sleeve 210 may be secured by coupler 220 to maintain an angle $\alpha$ with the longitudinal axis of the artery. Angle $\alpha$ is an acute angle (i.e., less than) 90°, optionally between 20° and 60°, optionally about 40°.

Coupler 220 includes a mount 223, an adapter 222 and an intermediate portion 221. Mount 223 may be shaped and sized with a contour having a diameter Da that is substantially the same as the artery outer diameter, so that it can coincide and nest thereupon. Intermediate portion 221 may include an acutely rounded portion 224 having a radius of curvature R (either variable or fixed). Rounded portion 224 also determines the angle $\alpha$. Optionally, radius of curvature R is 0.1 mm to 20 mm in length, optionally 0.25 mm to 4 mm, optionally 0.5 mm to 2.5 mm, or higher, or lower, or in an intermediate size.

Figure 4A:
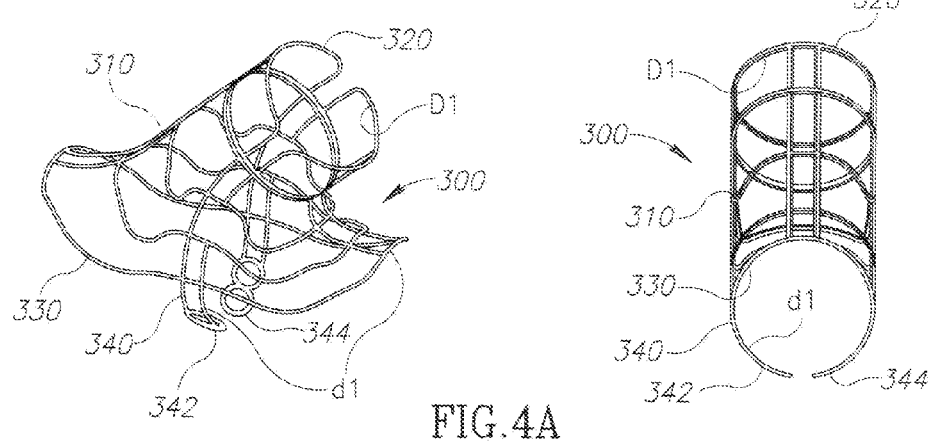
FIG. 4A schematically illustrates, in perspective views, an exemplary coupler, in accordance with some embodiments of the present invention.
Figure 4B:
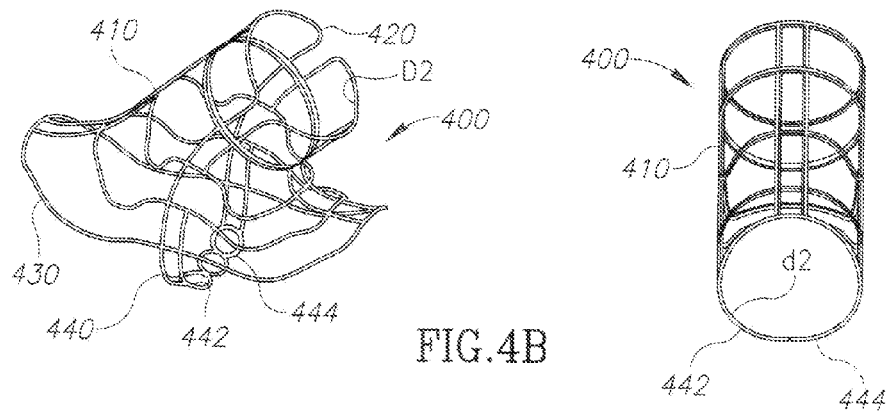
FIG. 4B schematically illustrates, in perspective views, an exemplary coupler, in accordance with some embodiments of the present invention.
Figure 4C:
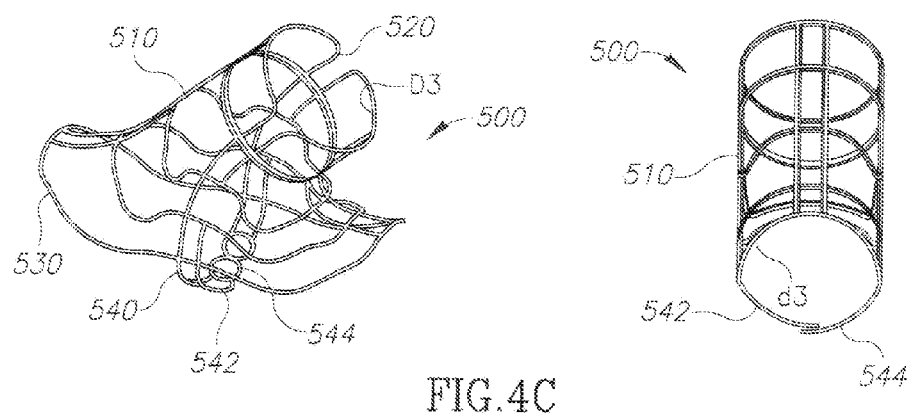
FIG. 4C schematically illustrates, in perspective views, an exemplary coupler, in accordance with some embodiments of the present invention.

FIGS. 4A-C schematically illustrate exemplary couplers 300, 400 and 500, which are, respectively, similar or identical to coupler 120, with the exception of differences in respective braces 340, 440 and 540.

FIG. 4A shows a first perspective view (left) and a second perspective view (right) of coupler 300. Coupler 300 includes a mount 330 contoured to coincide and nest upon an artery portion having a diameter d1, an adapter 320 comprising a cylindrical shape enclosing a diameter D1 being equal to or greater than the outer boundaries of a fistula vein segment, and an intermediate portion 310 gradually changing in shape and surface orientation between mount 330 and adapter 320. Brace 340 may include two elastic legs 342 and 344, shown in a nonstressed formation, enclosing diameter d1 in which they are not in contact. Such a design allows a relatively simpler deploying and securing the coupler 300 to arteries of slightly different sizes. Legs 342 and 344 may also be bonded or sutured together.

FIG. 4B shows a first perspective view (left) and a second perspective view (right) of coupler 400. Coupler 400 includes a mount 430 contoured to coincide and nest upon an artery portion having a diameter d2, an adapter 420 comprising a cylindrical shape enclosing a diameter D2 being equal or greater than outer boundaries of a fistula vein segment, and an intermediate portion 410 gradually changing in shape and surface orientation between mount 430 and the adapter 420. Brace 440 may include two elastic legs 442 and 444, shown in a nonstressed formation, enclosing a diameter d2 in which they are in contact and closing a complete circle. Such a design allows a stiffer embracing of an artery having a diameter similar or identical to d2.

FIG. 4C shows a first perspective view (left) and a second perspective view (right) of coupler 500. Coupler 500 includes a mount 530 contoured to coincide and nest upon an artery portion having a diameter d3, an adapter 520 comprising a cylindrical shape enclosing a diameter D3 being equal or greater than outer boundaries of a fistula vein segment, and an intermediate portion 510 gradually changing in shape and surface orientation between mount 530 and adapter 520. Brace 540 may include two elastic legs 542 and 544 shown in a nonstressed formation enclosing diameter d3 in which they are partly overlaying one on the other. Such a design allows a stiffer embrace of the artery. Additionally, brace 540 may deform the artery portion to a non-circular cross section, which may improve blood flow at or near the deformation.

In some alternative embodiments of the invention, any of brace 340, 440 and 540, are at least partially plastically deformable and/or can be transformed from elastic conditions to plastic conditions by applying enough force thereto, so that a user may define a needed enclosing diameter different from d1, d2, and/or d3, respectively.

Any of coupler 300, 400 and 500 may be connected to a restrictor sleeve to provide a fistula join. Alternatively, a fistula join may include any of couplers 300, 400 and 500, without a restrictor sleeve.

Figure 5D:
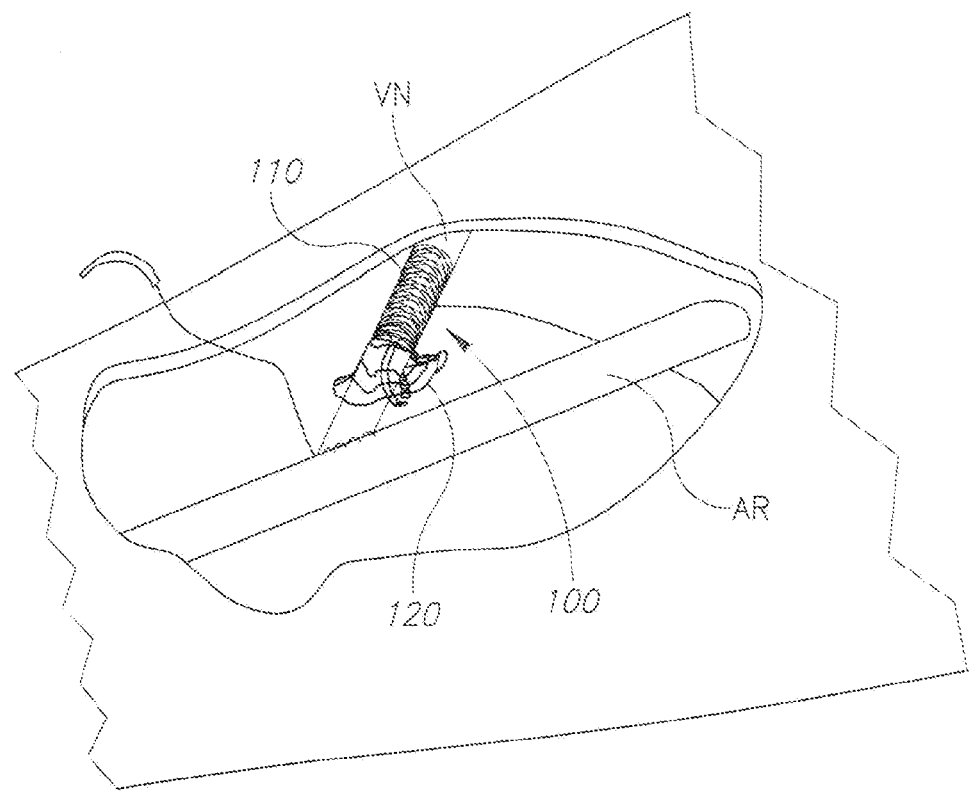
Figure 5E:
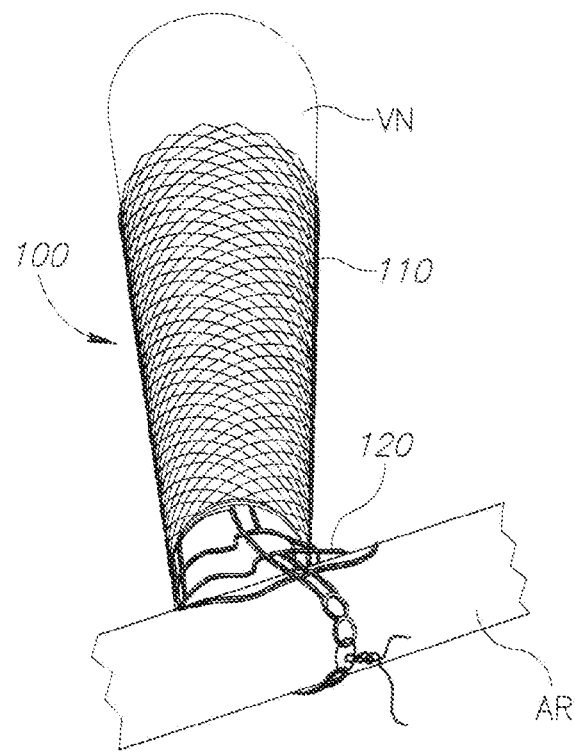

FIGS. 5A-E schematically illustrate steps that may be included in a method of deploying and implanting a fistula join 100 (as, for example, described with reference to FIGS. 2A-B). The method may comprise the steps of: providing a fistula join 100 comprising a coupler 120 connected to a restrictor sleeve 110 having a lumen 112; selecting a vein VN and an artery AR (FIG. 5A); transecting the vein VN and selecting the vein segment VN leading to the heart (FIG. 5B); passing the free end of the vein segment VN completely through lumen 112 so that the open end of vein segment VN protrudes from coupler 120 (FIG. 5C); anastomosing the open end of vein segment VN to the side of artery AR, as known in common practice, to create an arteriovenous junction having a fistula (FIG. 5D); and passing fistula join 100 through vein VN to attach coupler 120 to artery AR around the fistula (FIG. 5E).

The above method may include additional steps. For example, the free end of vein segment VN may be trimmed at an angle to facilitate the joining of vein VN to artery AR at a desired join angle (FIG. 5C).

Additionally or alternatively, if restrictor sleeve 110 is initially presented in a compressed state having a greater lumen diameter, then the method may include the further step, prior to or following the step of attaching coupler 120 to artery AR shown in FIG. 5E, of configuring restrictor sleeve 110 to the non-compressed state having a smaller lumen diameter to firmly enclose vein segment VN in the lumen of restrictor sleeve 110. Additionally or alternatively, restrictor sleeve 110 may be sutured and/or bonded in position onto vein segment VN.

Additionally or alternatively, if coupler 120 includes a brace, the method may include the further step, following the step of attaching coupler 120 to the artery AR shown in FIG. 5E, of closing the brace around artery AR. The method may include a yet further step of securing the closed state of brace 125 with a suture.

In certain alternative embodiments of the invention, the step of passing, nesting or securing coupler 120 onto artery AR may be performed before the step of performing the anastomosis. Such a procedure allows, for example, for the desired join angle to be secured in advance of as well as during the performance of anastomosis.

Such an alternative method may comprise the steps of: securing a coupler 120 to an artery AR; transecting a vein VN and selecting the vein segment VN leading to the heart; ensheathing vein segment VN with a restrictor sleeve 110 so that the free end of vein segment VN protrudes from inlet 114; connecting inlet 114 to adapter 123 of the coupler 120 to construct a fistula join 100; anastomosing the free end of vein segment VN to the side of artery AR through fistula join 100 to create an arteriovenous junction having a fistula.

Another alternative method may comprise the steps of: securing a coupler 120 to an artery AR; connecting the inlet 114 of a restrictor sleeve 110 to adapter 123 of coupler 120 to construct a fistula join 100; transecting a vein VN and selecting vein segment VN leading to the heart; ensheathing vein segment VN with a restrictor sleeve 110 so that the free end of vein segment VN protrudes from inlet 114 and is apposed to artery AR; anastomosing the free end of vein segment VN to the side of artery AR through fistula join 100 to create an arteriovenous junction having a fistula.

Optionally, the ensheathing of vein segment VN with restrictor sleeve 110 includes passing restrictor sleeve 110 through a vein VN in a compressed state having a greater lumen diameter, then configuring restrictor sleeve 110 into the non-compressed state having a smaller lumen diameter that is smaller, larger, or substantially the same as the external diameter of the vein VN. Additionally or alternatively, restrictor sleeve 110 may be sutured and/or glued in position over vein segment VN.

As a further alternative, the methods described above may be performed without a restrictor sleeve, for example with a fistula join 100 comprising only coupler 120 or coupler 300, 400 or 500, as described hereinabove. Alternatively, the methods described above may be performed with a restrictor sleeve, without a coupler.

Any of the above methods may serve to configure any one or any combination of two or more of the join angle, the first constrained shape and the second constrained shape (where a restrictor sleeve is used). Additionally or alternatively, any of the above methods may serve to enhance laminar flow of blood through the fistula and/or in at least one of the fistula artery and fistula vein in the vicinity of the fistula. Additionally or alternatively, any of the above methods may serve to moderate blood pressure in the fistula artery or fistula vein in the vicinity of the fistula.

As described herein, the fistula join of the embodiments of the invention serves to configure any one of or any combination of the join angle, the first constrained shape to second constrained shape (where a the fistula join includes a restrictor sleeve) in the vasculature at or in the vicinity of a fistula to improve blood flow characteristics therethrough. Such improved blood flow characteristics include diminishing turbulent blood flow, increasing laminar blood flow, increasing hemodynamic shear stress, and/or decreasing the average Reynolds number of the blood flow. As used herein, improved blood flow may refer to the blood flow exhibiting fewer, smaller or weaker zones of turbulent/slow flow overall, or fewer, smaller or weaker zones of turbulent/slow flow located on the luminal surface at the fistula or in the vein segment in the vicinity of the fistula (for example within about 3 cm from the fistula), which may be associated with the development of stenosis and neointimal hyperplasia.

FIGS. 6A-B, 7A-B, 8A-C and 9 show images of computer simulations of blood flow from an artery AN through a fistula to a vein VN in a vein-end-to-artery-side configuration. Flow velocity is represented in a red-to-blue color gradient, where regions of high velocity/laminar flow are shown in red, regions of low velocity/turbulent flow are shown in blue, and regions of intermediate flow are shown in yellow/green. As presented herein, the figures have been converted to grayscale, with regions of higher velocity/laminar flow being darker and regions of lower velocity/turbulent flow being lighter.

Various parameters were considered in the simulation, including: bulk blood flow rate (in mL/minute) through vein VN and artery AN on both sides of the arteriovenous junction; artery diameter, vein diameter(s), arteriotomy length and the join angle (defined as the acute angle at which the vein and the artery connect). The vein diameter was optionally variable over the distance from the arteriovenous junction. In the simulations presented, the vein was configured to either be cylindrical, with the diameter remaining constant along the length of the vein, or have an initial conical segment with the diameter increasing at a constant rate along the length of the vein for a defined distance CL (alternatively referred to herein as "cone length") starting from the fistula then become cylindrical. The initial diameter of the vein, at the circular cross section of the vein in the vicinity of the fistula (e.g., corresponding to the location of line 804 in FIG. 6A), was typically set to be equal to the diameter of artery AN (e.g., corresponding to line 802 in FIG. 6A), and the terminal diameter of the vein at and beyond the end of the initial conical segment (e.g., at line 806 in FIG. 6A) was set as being a defined multiple of the diameter of the artery (ranging from being 1.2 to 2 times the diameter of artery AN). The artery diameter ranged from about 2.5 mm to about 4 mm, depending on whether a radial artery or a brachial artery was simulated.

Referring now to FIGS. 6A-B and 7A-B, we studied blood flow in simulations of maturing radiocephalic and brachiocephalic junctions. The maturation of the junctions was represented by: 1) increasing venous flow rate; and 2) increasing vein diameter as expressed as an increasing vein/artery diameter ratio. The radiocephalic junction was configured as having an artery diameter of 2.9 mm and the brachiocephalic junction was configured as having an artery diameter of 4 mm. The vein diameter was configured to increase from 1.2 times the arterial diameter to 2 times the arterial diameter. The initial 10 mm of the vein segment most proximal to the fistula was configured as having a conical shape, with the remaining vein segment being cylindrical in shape. (The conical shape may be slight, especially in cases where the differences between the initial and terminal diameters are small. Thus, the conical segment may not be readily apparent in the figures.) The arteriotomy was set to be 5 mm. The join angle was set to be 45°.

We found that, across the two artery types and a range of flow rates, fistulas having a vein/artery diameter ratio of about 1.4 demonstrated the least turbulence overall. The blood flow in simulated fistulas having a lower vein/artery diameter ratio, e.g., 1.2, as well as the blood flow in simulated fistulas having a higher vein/artery diameter ratio, e.g., 1.6, was in general more turbulent compared to blood flow in simulated fistulas having a vein/artery diameter ratio of 1.4. In particular, the simulated blood flow exhibited fewer, smaller and weaker zones of turbulent flow associated with the development of stenosis and neointimal hyperplasia, i.e., located on the luminal surface at the fistula or in the vein segment proximal to the fistula (for example, within about 3 cm from the fistula).

FIGS. 6A-B show exemplary images of blood flow through a simulation of a developing radiocephalic junction. In the transition between FIG. 6A and FIG. 6B, the vein/artery diameter ratio changed from 1.2 to 1.4 with the other parameters remaining the same (including the blood flow rate in vein VN, which was maintained at 265 mL/minute). Referring to FIG. 6A, the initial vein diameter, e.g., at line 804 is equal to the artery diameter, e.g., at line 802, and the terminal vein diameter, e.g., at line 806, is 1.2 times the artery diameter. Referring to FIG. 6B, the initial vein diameter, e.g., at line 814, is equal to the artery diameter, e.g., at line 812, and the terminal vein diameter, e.g., at line 816 is 1.4 times the artery diameter.

The improvement of blood flow in the junction having a vein/artery diameter ratio of 1.4 (FIG. 6B) compared to a vein/artery diameter ratio of 1.2 (FIG. 6A), can been seen by the reduction in the size of regions of turbulent blood flow (light) combined with the increase in size of regions of laminar blood flow (dark). This improvement in blood flow is particularly apparent where turbulent region 704 along the lumen of vein VN having a vein/artery diameter ratio of 1.2 (FIG. 6A) is larger than the corresponding turbulent region 707 along the lumen of vein VN having a vein/artery diameter ration of 1.4 (FIG. 6B). A similar reduction in turbulent flow is apparent when comparing the size of turbulent flow region turbulent region 702 (FIG. 6A) with corresponding turbulent region 706 (FIG. 6B).

Having a conical segment in the initial portion of the fistula vein with a larger vein/artery diameter ratio does not necessarily improve blood flow through the arteriovenous junction. FIGS. 7A-B show the same simulated radiocephalic junction exhibiting increased turbulence when the vein/artery ratio increased from 1.4 to 1.6, while the other parameters remained unchanged (including the blood flow rate at vein VN, which was maintained at 495 mL/minute). Referring to FIG. 7A, the initial vein diameter, e.g., at line 824, is equal to the artery diameter, e.g., at line 822, and the terminal vein diameter, e.g., at line 826, is 1.4 times the artery diameter. Referring to FIG. 7B, the initial vein diameter, e.g., at line 834, is equal to the artery diameter, e.g., at line 832, and the terminal vein diameter, e.g., at line 836 is 1.6 times the artery diameter.

The degradation of blood flow in the junction having a vein/artery diameter ratio of 1.6 (FIG. 7B) compared to a vein/artery diameter ratio of 1.4 (FIG. 7A), is particularly apparent where turbulent region 708 along the lumen of vein VN having a vein/artery diameter ratio of 1.4 (FIG. 6A) is smaller than the corresponding turbulent region 710 along the lumen of vein VN having a vein/artery diameter ration of 1.6 (FIG. 6B).

We also found that a conical segment having a length of about 15 mm was particularly beneficial, across a range of other conditions such as artery diameter, blood flow rate and vein/artery diameter ratios, in improving blood flow through simulated arteriovenous junctions. Referring now to FIGS. 8A-C, we tested four different lengths of the initial conical segment: 0 mm (completely cylindrical in shape; not shown), 15 mm (FIG. 8A; cone length CL1 defined by lines 842 and 844), 20 mm (FIG. 8B; cone length CL2 defined by lines 862 and 864) and 25 mm (FIG. 8C; cone length CL3 defined by lines 882 and 884). The simulated junctions were configured as a brachiocephalic junction having the same following parameters: an artery diameter of 3.5 mm, a vein/artery diameter ratio of 1.29 (with the terminal vein diameter after the conical segment being 4.5 mm), a join angle of 40°, an arteriotomy length of 5 mm, and an initial arterial blood flow rate of 200 mL/minute. Vein segment VN beyond the conical segment was configured to be cylindrical in shape. The improvement in blood flow in vein VN having the 15 mm conical region (FIG. 8A) is particularly apparent at turbulent region (light) region 712, which was smaller than corresponding turbulent region 714 of FIG. 8B where the conical region is 20 mm, and also smaller than corresponding turbulent region 716 of FIG. 8C where the conical region is 25 mm.

Further simulations, similarly performed, demonstrated that a fistula join angle of about 40° was particularly beneficial in reducing turbulent blood flow. That is, simulated junctions having a join angle of 40°, across various conditions such as artery diameter, blood flow rate and vein/artery diameter ratios, generally demonstrated less turbulent blood flow when compared to simulated junctions having a join angle of 20° or 60°.

Referring now to FIG. 9, we also generated a simulated junction in a conventional configuration having a join angle of 15° and a fully cylindrical vein (without an initial conical segment), which is one of various configurations that an arteriovenous junction may typically take without implantation of structural supports. The remaining parameters generally match the simulations shown in FIGS. 8A-C: an artery diameter of 3.5 mm, a vein/artery diameter ratio of 1.29 (with the vein diameter being 4.5 mm), an arteriotomy length of 6 mm and an initial arterial blood flow rate of 200 mL/minute. This conventional junction exhibited a higher level of turbulent flow overall, and further exhibited two focused regions of turbulent flow 718, 720 juxtaposing with the fistula. As such, any one of the above-described geometrical features, such as a join angle of 40° or an initial conical segment in the vein will improve blood flow at or near an arteriovenous fistula over conventional conditions.

Based on the simulation studies as described above, certain embodiments of the invention provide for a fistula join operable to shape or constrain the fistula or the surrounding vasculature to have one or more of the following preferred parameters: a join angle of about 40°; a vein/artery diameter ratio of about 1.4; or a fistula vein segment being conical in shape at the initial approximately 15 mm from the fistula, then optionally being cylindrical in shape.

Certain embodiments of the invention further provide for a preferred fistula join comprising: a restrictor sleeve having a mixed conical/cylindrical shape, the initial segment of about 15 mm starting from the inlet being conical and the remainder being cylindrical, and the outlet diameter being larger than the inlet diameter by a factor of about 1.4; and a coupler having an adapter configured to connect with the inlet and secure the restrictor sleeve at a join angle of about 40°.

In the description and claims of the present application, each of the verbs, "comprise" "include" and "have", and conjugates thereof, are used to indicate that the object or objects of the verb are not necessarily a complete listing of components, elements or parts of the subject or subjects of the verb.

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims.

The invention claimed is:

1. A method of configuring blood vessels at an anastomosis, the method comprising:
ensheathing a segment of a transected first blood vessel in a lumen of a sleeve having an end connected via an adapter to a mount, so that an open end of the first blood vessel segment protrudes from the sleeve end and the mount,
wherein the mount has a saddle-like shape comprising a convex face surface, a concave face surface configured to be seated on and coupled to a second blood vessel, the mount having a first side and a second side;
suturing edges of an incision made in the second blood vessel to the open end of the first blood vessel segment to create an anastomosis;
sliding the sleeve and the adapter along the first blood vessel to seat the mount onto the second blood vessel at the anastomosis, and
coupling a brace, having a first side and second side, to the mount, the first side of the brace being coupled to the first side of the mount, and the second side of the brace coupled to the second side of the mount, such that the mount and the brace together encircle the second blood vessel, to secure the mount to the second blood vessel.

2. The method according to claim 1, wherein seating the mount further comprises suturing or bonding the mount to the second blood vessel.

3. The method according to claim 1 further comprising:
configuring the sleeve from a longitudinally compressed state having a first diameter greater than that of the first blood vessel to a longitudinally expanded state having a diameter smaller than that of the first blood vessel in order to enclose the portion of the first blood vessel firmly in the lumen of the sleeve.

4. The method according to claim 1, wherein the mount is configured to deform the second blood vessel to have a non-circular cross section.

5. The method according to claim 1, wherein the mount is configured to hold the sleeve, relative to the second blood vessel, at an acute angle that is greater than about 20 degrees and less than about 60 degrees.

6. The method according to claim 5, wherein the mount is shaped to impose a rounded contour at the acute angle.

7. The method according to claim 1, wherein the first and second vessels are selected or configured such that, upon completion of the anastomosis and initiation of blood flow through the anastomosis, blood flow through the first vessel ensheathed by the sleeve is directed away from the second vessel.

8. A method of configuring blood vessels at an anastomosis, the method comprising:
ensheathing a segment of a transected first blood vessel in a lumen of a sleeve;
connecting, to the sleeve end, a mount via an adapter, the mount having a saddle-like shape comprising a convex face surface and a concave face surface configured to be seated on and coupled to a second blood vessel, the mount having a first side and a second side, whereby the open end of the segment protrudes from the mount;
suturing edges of an incision made in the second blood vessel to the open end of the segment to create an anastomosis;
seating the concave face surface of the mount to the second blood vessel at a site of anastomosis; and
coupling a brace, having a first side and a second side, to the mount, the first side of the brace being coupled to the first side of the mount, and the second side of the brace coupled to the second side of the mount, such that the mount and brace together encircle the second blood vessel, to secure the mount to the second blood vessel.

9. The method according to claim 8, wherein the method comprises the sequential steps of:
(A) connecting the adapter to the sleeve end;

(B) ensheathing the first blood vessel segment in the sleeve, the adapter, and the mount so that the open end of the segment protrudes from the sleeve end, the adapter, and the mount;

(C) suturing the open end of the first blood vessel to incision edges in the second blood vessel to create an anastomosis; and (D) seating the mount onto the second blood vessel so that the open end protruding from the mount is apposed to the site of anastomosis.

10. The method according to claim 8 wherein the method comprises the sequential steps of:
connecting the adapter to the sleeve end;
seating the mount onto the second blood vessel at the site of anastomosis;
ensheathing the segment of the transected first blood vessel in the sleeve connected to the adapter so that the open end of the segment protrudes from the sleeve end and the mount, and is apposed to the second blood vessel at the site of anastomosis; and
suturing the open end to the incisions edges made in the second blood vessel to create an anastomosis.

11. The method according to claim 8 wherein the method comprises the sequential steps of:
seating the mount onto the second blood vessel at the site of anastomosis;
ensheathing the first blood vessel segment in the sleeve so that the open end of the segment protrudes from the sleeve end;
connecting the adapter to the sleeve end so that the open end protrudes from the adapter and is apposed to the second blood vessel at the site of anastomosis; and
suturing the open end to the incision edges in the second blood vessel to create an anastomosis.

12. The method according to claim 8, wherein the method comprises the sequential steps of:
ensheathing the first blood vessel segment in the sleeve so that the open end of the segment protrudes from the sleeve end;
connecting the adapter to the sleeve end so that the open end of the segment protrudes from the adapter;
suturing the open end of the first blood vessel to the incision edges in the second blood vessel to create an anastomosis; and
coupling the adapter onto the second blood vessel.

13. The method according to claim 8, wherein seating the mount further comprises suturing or bonding the coupler to the second blood vessel.

14. The method according to claim 8 further comprising:
configuring the sleeve from a longitudinally compressed state having a first diameter greater than that of the first blood vessel to a longitudinally expanded state having a diameter smaller than that of the first blood vessel in order to enclose the portion of the first blood vessel firmly in the lumen of the sleeve.

15. The method according to claim 8, wherein the mount is configured to deform the second blood vessel to have a non-circular cross section.

16. The method according to claim 8, wherein the adapter is configured to hold the sleeve, relative to the second blood vessel, at an acute angle that is greater than about 20 degrees and less than about 60 degrees.

17. The method according to claim 16, wherein the adapter is shaped to impose a rounded contour at the acute angle.

18. A method of configuring blood vessels at an anastomosis, the method comprising:
ensheathing a segment of a transected first blood vessel in a lumen of a sleeve, having an end connected to a mount, so that an open end of the segment protrudes from sleeve end and the mount;
suturing edges of an incision made in a second blood vessel to the open end of the first blood vessel to create the anastomosis;
sliding the sleeve and mount along the first blood vessel to position the sleeve at the anastomosis, and
coupling the mount to seat it onto the second blood vessel at the anastomosis; and
coupling a brace to the mount and the second blood vessel, such that the mount and the brace together encircle the second blood vessel, to secure the mount to the second blood vessel.

19. The method according to claim 18 further comprising suturing or bonding a portion of the sleeve or mount to the second blood vessel.

20. The method according to claim 18 further comprising:
after positioning the sleeve at the anastomosis, configuring the sleeve from a longitudinally compressed state having a first diameter greater than that of the first blood vessel to a longitudinally expanded state having a diameter smaller than that of the first blood vessel in order to enclose the portion of the first blood vessel firmly in the lumen of the sleeve.

21. A method of configuring blood vessels at an anastomosis, the method comprising:
ensheathing a segment of a transected first blood vessel in a lumen of a sleeve having an end connected via an adapter to a mount, so that an open end of the first blood vessel segment protrudes from the sleeve end and the mount,
wherein the mount has a saddle-like shape comprising a convex face surface, a concave face surface configured to be seated on and coupled to a second blood vessel;
suturing edges of an incision made in the second blood vessel to the open end of the first blood vessel segment to create an anastomosis;
sliding the sleeve and the adapter along the first blood vessel to seat the mount onto the second blood vessel at the anastomosis, and
coupling a brace to the mount, wherein the brace together with the mount, encircles the exterior of the second blood vessel, such that the mount and the brace together secure the mount to the second blood vessel.

22. A method of configuring blood vessels at an anastomosis, the method comprising:
ensheathing a segment of a transected first blood vessel in a lumen of a sleeve having an end connected via an adapter to a mount, so that an open end of the first blood vessel segment protrudes from the sleeve end and the mount,
wherein the mount has a saddle-like shape comprising a convex face surface, a concave face surface configured to be seated on and coupled to a second blood vessel;
suturing edges of an incision made in the second blood vessel to the open end of the first blood vessel segment to create an anastomosis;
sliding the sleeve and the adapter along the first blood vessel to seat the mount onto the second blood vessel at the anastomosis, and coupling a brace to the mount, wherein the mount and the brace together encircles the exterior of the second blood vessel so as to secure the mount to the second blood vessel.

* * * * *